United States Patent
Al-Qahtani et al.

(10) Patent No.: US 10,927,058 B2
(45) Date of Patent: Feb. 23, 2021

(54) SYSTEMS AND METHODS RELATED TO THE SYNGAS TO OLEFIN PROCESS

(71) Applicant: SABIC Global Technologies B.V., Bergen op Zoom (NL)

(72) Inventors: Thabet Mohammed Al-Qahtani, Riyadh (SA); Khalid Karim, Riyadh (SA); Mubarik Ali Bashir, Riyadh (SA); Ali Al-Hammad, Riyadh (SA); Labeeb Chaudhary Ahmed, Riyadh (SA); Saud Al-Khudeer, Riyadh (SA); Abdullah Turki Al-Jaloud, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/573,607

(22) PCT Filed: May 12, 2016

(86) PCT No.: PCT/IB2016/052752
§ 371 (c)(1),
(2) Date: Nov. 13, 2017

(87) PCT Pub. No.: WO2016/185334
PCT Pub. Date: Nov. 24, 2016

(65) Prior Publication Data
US 2018/0118639 A1    May 3, 2018

Related U.S. Application Data

(60) Provisional application No. 62/161,997, filed on May 15, 2015.

(51) Int. Cl.
*C07C 7/04* (2006.01)
*C07C 5/48* (2006.01)
(Continued)

(52) U.S. Cl.
CPC ........ *C07C 5/48* (2013.01); *B01J 8/04* (2013.01); *B01J 8/08* (2013.01); *B01J 8/24* (2013.01);
(Continued)

(58) Field of Classification Search
CPC .... C10G 2300/1022; C10G 2/30; C10G 2/31; C10G 2/32; C10G 9/00; C10G 11/00
(Continued)

(56) References Cited

U.S. PATENT DOCUMENTS 2,506,065 A    5/1950  Alfred
2,678,263 A *  5/1954  Glazier ................. C10L 1/06
                                              208/57
(Continued)

FOREIGN PATENT DOCUMENTS

CN    101434507 A  *  5/2009
CN    102604677       7/2012
(Continued)

OTHER PUBLICATIONS

Nijs, H. H.; Jacobs, P. A. "On-Line Single Run Analysis of Effluents from a Fischer-Tropsch Reactor", Journal of Chromatographic Science (1981), 19; pp. 40-45. (Year: 1981).*
(Continued)

*Primary Examiner* — Philip Y Louie
(74) *Attorney, Agent, or Firm* — Norton Rose Fulbright US LLP (57) ABSTRACT

Disclosed herein is a system and method capable of producing butadiene from a product stream.

16 Claims, 1 Drawing Sheet

(51) Int. Cl.

| | |
|---|---|
| *C10G 63/04* | (2006.01) |
| *C10G 35/095* | (2006.01) |
| *C10G 2/00* | (2006.01) |
| *C10G 47/00* | (2006.01) |
| *B01J 8/04* | (2006.01) |
| *B01J 8/08* | (2006.01) |
| *B01J 8/24* | (2006.01) |
| *C07C 2/00* | (2006.01) |
| *C07C 4/16* | (2006.01) |
| *C07C 7/00* | (2006.01) |

(52) U.S. Cl.
CPC ............... *C07C 2/00* (2013.01); *C07C 4/16* (2013.01); *C07C 7/005* (2013.01); *C07C 7/04* (2013.01); *C10G 2/30* (2013.01); *C10G 35/095* (2013.01); *C10G 47/00* (2013.01); *C10G 63/04* (2013.01); *C10G 2300/1022* (2013.01); *C10G 2400/20* (2013.01); *C10G 2400/30* (2013.01)

(58) Field of Classification Search
USPC .................... 208/106–108, 113; 585/601
See application file for complete search history.

(56) References Cited

U.S. PATENT DOCUMENTS

| | | | |
|---|---|---|---|
| 2,850,550 A | 9/1958 | Reinmuth | |
| 3,284,526 A | 11/1966 | Frayer et al. | |
| 3,914,332 A | 10/1975 | Dickason | |
| 4,088,671 A | 5/1978 | Kobylinski | |
| 4,207,248 A | 6/1980 | Butter et al. | |
| 4,463,206 A | 7/1984 | Derrien et al. | |
| 5,306,854 A | 4/1994 | Choudhary et al. | |
| 5,785,739 A | 7/1998 | Baker | |
| 5,791,161 A | 8/1998 | Manley | |
| 5,831,108 A | 11/1998 | Grubbs et al. | |
| 5,968,343 A | 10/1999 | Drake et al. | |
| 5,990,370 A | 11/1999 | Sims | |
| 6,077,985 A | 6/2000 | Stork | |
| 6,291,734 B1 | 9/2001 | Stork | |
| 6,392,109 B1 | 5/2002 | O'Rear et al. | |
| 7,417,173 B2 | 8/2008 | Crone et al. | |
| 7,554,002 B2 | 6/2009 | Pham Duc | |
| 8,066,868 B1 * | 11/2011 | Zimmermann | C10G 21/00 208/100 |
| 8,222,472 B2 * | 7/2012 | Chung | C07C 5/42 585/616 |
| 8,268,897 B2 | 9/2012 | Huffman | |
| 8,309,616 B2 | 11/2012 | Huffman | |
| 2005/0171311 A1 | 8/2005 | Schindler et al. | |
| 2007/0249793 A1 | 10/2007 | Vanderbilt et al. | |
| 2008/0312347 A1 * | 12/2008 | Ernst | C01B 3/36 518/702 |
| 2009/0156870 A1 * | 6/2009 | Lauritzen | C07C 2/66 585/24 |
| 2010/0069589 A1 | 3/2010 | Bradin | |
| 2011/0105811 A1 * | 5/2011 | O'Rear | C10G 2/32 585/1 |
| 2011/0207979 A1 * | 8/2011 | Kim | C10G 11/02 585/256 |
| 2012/0088944 A1 | 4/2012 | Buijs et al. | |
| 2013/0225884 A1 * | 8/2013 | Weinberger | F25J 3/0219 585/16 |
| 2013/0248419 A1 | 9/2013 | Abba et al. | |
| 2014/0128486 A1 | 5/2014 | Karim et al. | |
| 2014/0200377 A1 | 7/2014 | Yanagawa et al. | |
| 2018/0044445 A1 | 2/2018 | Al-Shammari et al. | |
| 2018/0134966 A1 | 5/2018 | Ai-Qahtani et al. | |

FOREIGN PATENT DOCUMENTS

| | | | |
|---|---|---|---|
| CN | 103626898 | 3/2014 | |
| EP | 0082702 | 6/1983 | |
| EP | 1035094 | 9/2013 | |
| WO | WO 2013/182534 | 12/2013 | |
| WO | WO-2013182534 A1 * | 12/2013 | .......... B01J 35/0006 |
| WO | WO 2016/132293 | 8/2016 | |
| WO | WO 2016/185335 | 11/2016 | |

OTHER PUBLICATIONS

Park, J.-H. et. al. "Oxidative dehydrogenation of 1-butene to 1,3-butadiene over BiFe0.65NixMo oxide catalysts; Effect of nickel content", Catalysis Communications (2013), 31; pp. 76-80. (Year: 2013).*
Zhang, J. et. al. "Surface-Modified Carbon Nanotubes Catalyze Oxidative Dehydrogenation of n-Butane"; Science (2008), 322; pp. 73-77. (Year: 2008).*
Sterrett, J. S. et. al. "Kinetics of the Oxidative Dehydrogenation of Butene to Butadiene over a Ferrite Catalyst", Ind. Eng. Chem., (1974), 13; pp. 54-59. (Year: 1974).*
CN101434507 English Translation obtained from Espacenet, pp. 1-11 (Year: 2020).*
Perry et al., Distillation Section 13, Perry's Chemical Engineers' Handbook, McGraw-Hill, 2008, pp. 13-01-13-02 and 13-59-13-67. (Year: 2008).*
International Search Report and Written Opinion dated May 17, 2016 by the International Searching Authority for International Patent Application No. PCT/IB2016/050825, filed Feb. 16, 2016 and published as WO 2016/132293 on Aug. 25, 2016 (Applicant—Sabic Global Technologies B.V.) (8 pages).
International Preliminary Report on Patentability dated Aug. 22, 2017 by the International Searching Authority for International Patent Application No. PCT/IB2016/050825, filed Feb. 16, 2016 and published as WO 2016/132293 on Aug. 25, 2016 (Applicant—Sabic Global Technologies B.V.) (5 pages).
International Search Report and Written Opinion dated Aug. 19, 2016 by the International Searching Authority for International Patent Application No. PCT/IB2016/052752, filed May 12, 2016 and published as WO 2016/185334 on Nov. 24, 2016 (Applicant—Sabic Global Technologies B.V.) (11 pages).
International Search Report and Written Opinion dated Aug. 19, 2016 by the International Searching Authority for International Patent Application No. PCT/IB2016/052753, filed May 12, 2016 and published as WO 2016/185335 on Nov. 24, 2016 (Applicant—Sabic Global Technologies B.V.) (9 pages).
International Preliminary Report on Patentability dated Nov. 21, 2017 by the International Searching Authority for International Application No. PCT/IB2016/052752, filed May 12, 2016 and published as WO 2016/185334 on Nov. 24, 2016 (Applicant—Sabic Global Technologies B.V.) (8 pages).
International Preliminary Report on Patentability dated Nov. 21, 2017 by the International Searching Authority for International Application No. PCT/IB2016/052753, filed May 12, 2016 and published as WO 2016/185335 on Nov. 24, 2016 (Applicant—Sabic Global Technologies B.V.) (7 pages).
Asaftei, I.V. et. al. "Aromatization of industrial feedstock mainly with butanes and butenes over HZSM-5 and Zn/HZSM-5 catalysts", Acta Chennica Lasi, 17 (2009), pp. 5-34. (Year: 2009).

* cited by examiner

SYSTEMS AND METHODS RELATED TO THE SYNGAS TO OLEFIN PROCESS

CROSS-REFERENCE TO RELATED APPLICATIONS

This is a U.S. National Phase Application of International Application No. PCT/IB2016/052752, filed May 12, 2016, which claims the benefit of U.S. Provisional Application No. 62/161,997, filed on May 15, 2015, which are both incorporated herein by reference in their entirety.

BACKGROUND

Syngas (mixtures of $H_2$ and CO) can be readily produced from either coal or methane (natural gas) by methods well known in the art and widely commercially practiced around the world. A number of well-known industrial processes use syngas for producing various oxygenated organic chemicals. The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprise iron or cobalt supported on alumina or titania. Promoters, such as, rhenium, zirconium, manganese, and the like, can sometimes be used with cobalt catalysts, to improve various aspects of catalytic performance. The products were typically gasoline-range hydrocarbon liquids having six or more carbon atoms, along with heavier hydrocarbon products. Today lower molecular weight C1-C5 hydrocarbons (paraffins and/or olefins) are desired and can be obtained from syngas via Fischer-Tropsch catalytic process.

There remains a long-term market need for new and improved methods for producing useful compound(s) from a Fischer-Tropsch process.

SUMMARY OF THE INVENTION

Disclosed herein is a system comprising: a) a Fischer-Tropsch reactor comprising a first inlet and a first outlet; b) a hydrocarbon separator comprising a second' outlet, a second" outlet, and a second'" outlet; c) a butadiene reactor comprising a third inlet and a third outlet; d) a C2-C3 olefin separator comprising a fourth inlet and a fourth outlet; and e) a C5+ hydrocarbon conversion reactor comprising a fifth inlet and a fifth outlet, wherein the Fischer-Tropsch reactor is in fluid communication with the hydrocarbon separator via a first connector, wherein the first connector is connected to the first outlet of the Fischer-Tropsch reactor and to the second inlet of the hydrocarbon separator, wherein the hydrocarbon separator is in fluid communication with the butadiene reactor via a second connector, wherein the second connector is connected to the second' outlet of the hydrocarbon separator and to the third inlet of the butadiene reactor, wherein the hydrocarbon separator is in fluid communication with the C2-C3 olefin separator via a third connector, wherein the third connector is connected to the second" outlet of the hydrocarbon separator and to the fourth inlet of the C2-C3 olefin separator, wherein the hydrocarbon separator is in fluid communication with the C5+ hydrocarbon conversion reactor via a fourth connector, wherein the fourth connector is connected to the second'" outlet of the hydrocarbon separator and to the fifth inlet of the C5+ hydrocarbon conversion reactor.

Also disclosed herein is a method comprising the steps of: a) providing a first product stream comprising a C2-C3 hydrocarbon stream, a C4 hydrocarbon stream comprising butane and butene, and a C5+ hydrocarbon stream; b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream; and e) converting at least a portion of the butene in the C4 hydrocarbon stream to butadiene.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying FIGURES, which are incorporated in and constitute a part of this specification, illustrate several aspects, and together with the description, serve to explain the principles of the invention.

Figure 1:
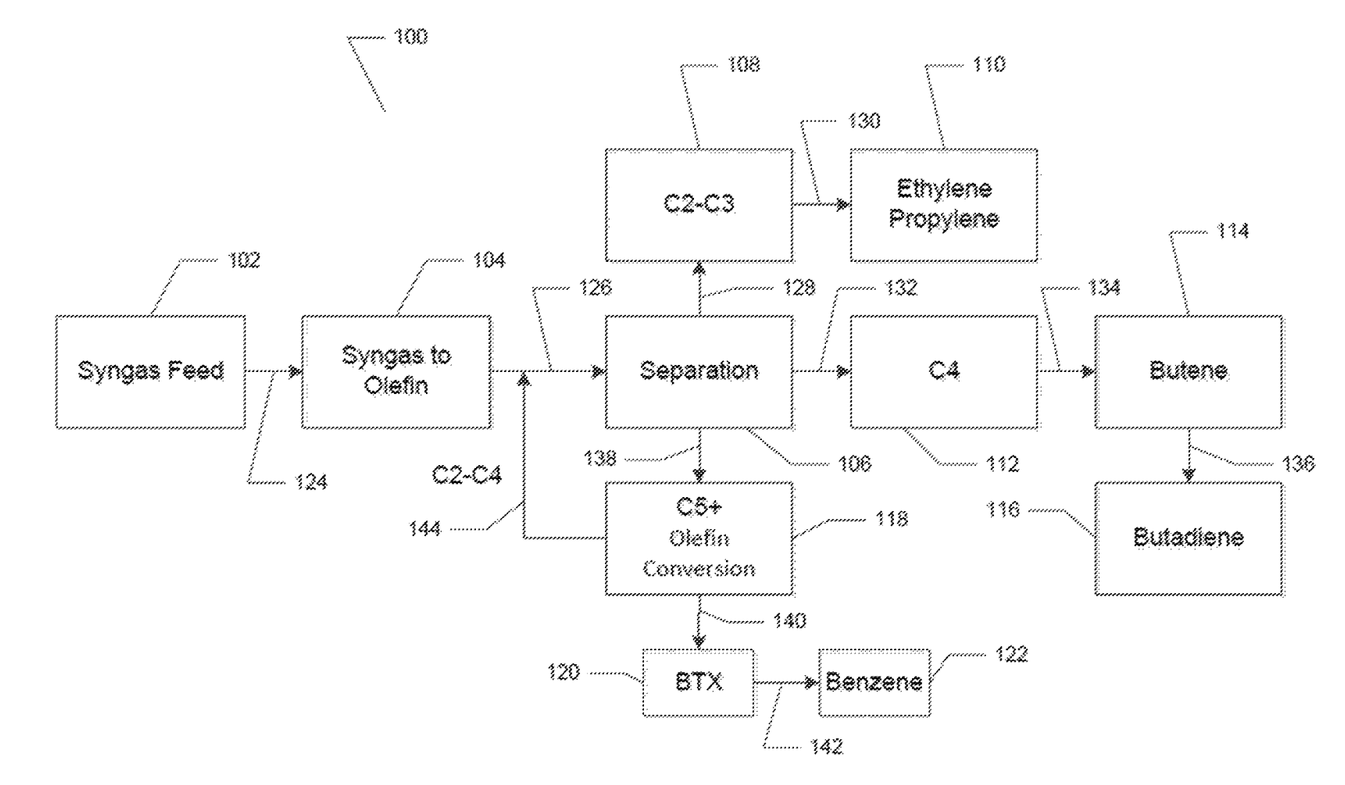
The FIGURE shows a flow diagram of a system and a method of one aspect disclosed herein.

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

1. Definitions

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a hydrocarbon" includes mixtures of hydrocarbons.

Ranges can be expressed herein as from " " one particular value, and/or to " " another particular value. When such a range is expressed, another aspect includes from the one particular value and/or to the other particular value. Similarly, when values are expressed as approximations, by use of the antecedent "," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

The term "butadiene" is used herein is interchangeable with 1,3-butadiene and has the chemical formula $C_4H_6$.

The term "butene" is used herein interchangeably with n-butene, which encompasses 1-butene or 2-butene, or a mixture thereof.

The term "BTX" as used herein is well known in the art and relates to a mixture of benzene, toluene and xylenes. As used herein, the term "chemical grade BTX" relates to a hydrocarbon mixture comprising less than 5 wt % of hydrocarbons other than benzene, toluene and xylenes, such as less than 4 wt % of hydrocarbons other than benzene, toluene and xylenes, such as less than 3 wt % of hydrocarbons other than benzene, toluene and xylenes, and such as less than 2.5 wt % of hydrocarbons other than benzene, toluene and xylenes.

The terms "xylene" and "xylenes" are used interchangeably herein. "Xylene" or "xylenes" refers to an aromatic hydrocarbon consisting of a benzene ring with two methyl groups. The methyl groups can be at various substituted positions of the benzene ring.

2. Fischer-Tropsch Catalytic Process

The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

Scheme 1

FT reaction: $nCO + 2nH_2 \rightarrow (CH_2)_n + H_2O$

Water Gas Shift Reaction (WGS): $CO + H_2O \rightarrow CO_2 + H_2$

Methanation $CO + H_2 \rightarrow CH_4 + H_2O$

The gases that are being mixed in the Fischer-Tropsch process described herein comprise $H_2$ and CO. The $H_2$/CO molar ratio of the feed gas can be from 0.5 to 4. For example, the $H_2$/CO molar ratio can be from 1.0 to 3.0, such as, for example, from 1.5 to 3.0, or in another example, from 1.5 to 2.5. It will be appreciated that the $H_2$/CO molar ratio can control the selectivity of the hydrocarbons that are being produced. The consumption molar ratio of $H_2$/CO is usually from about 1.0 to about 2.5, such as for example, from about 1.5 to 2.1. This ratio increases as long as the water gas shift reaction is active and, thus, the use of a feed ratio below the consumption ratio will result in a stable H/CO ratio during the reaction within an acceptable range (normally below 2). The $H_2$ and CO are catalytically reacted in a Fischer-Tropsch reaction.

A Fischer-Tropsch process that targets the production of olefins (i.e. C2-C10 olefins) is desired and such process can produce a significant amount of C4 hydrocarbons, including C4 paraffins and C4 olefins. As disclosed herein, a stream comprising C4 hydrocarbons can undergo processing to produce butadiene. Butadiene is an important monomer for the production of high molecular weight polymers. It is used extensively in the production of tires and other products in the automotive industry. It is also used extensively in the production of synthetic rubbers, such as styrene-butadiene rubber, nitrile-butadiene rubber, and styrene-butadiene latex. The system and method disclosed herein are capable of producing butadiene from a product stream produced in a Fischer-Tropsch Process.

As disclosed herein, a stream comprising C5+ hydrocarbons can undergo processing to produce benzene. Benzene is an important intermediate molecule to make other useful chemicals, such as, for example, ethylbenzene, cumene, cyclohexane, nitrobenzene, and alkylbenzene. For example, ethylbenzene is a precursor to styrene, for the production of high molecular weight polymers. Benzene is also used as a solvent and can be used to make various types of rubbers, lubricants, dyes, detergents, drugs, explosives, and pesticides. The system and method disclosed herein are capable of producing benzene from a product stream produced in a Fischer-Tropsch Process.

3. System

Disclosed herein is a system comprising: a) a Fischer-Tropsch reactor comprising a first inlet and a first outlet; b) a hydrocarbon separator comprising a second inlet, second' outlet, a second" outlet, and a second''' outlet; c) a butadiene reactor comprising a third inlet and a third outlet; d) a C2-C3 olefin separator comprising a fourth inlet and a fourth outlet; and e) a C5+ hydrocarbon conversion reactor comprising a fifth inlet and a fifth outlet, wherein the Fischer-Tropsch reactor is in fluid communication with the hydrocarbon separator via a first connector, wherein the first connector is connected to the first outlet of the Fischer-Tropsch reactor and to the second inlet of the hydrocarbon separator, wherein the hydrocarbon separator is in fluid communication with the butadiene reactor via a second connector, wherein the second connector is connected to the second' outlet of the hydrocarbon separator and to the third inlet of the butadiene reactor, wherein the hydrocarbon separator is in fluid communication with the C2-C3 olefin separator via a third connector, wherein the third connector is connected to the second" outlet of the hydrocarbon separator and to the fourth inlet of the C2-C3 olefin separator, wherein the hydrocarbon separator is in fluid communication with the C5+ hydrocarbon conversion reactor via a fourth connector, wherein the fourth connector is connected to the second'" outlet of the hydrocarbon separator and to the fifth inlet of the C5+ hydrocarbon conversion reactor.

It is understood that the sequence of reactors disclosed herein can vary based on the product distribution in the Fischer-Tropsch process, which produces olefins from syngas.

In one aspect, the system further comprises a syngas production reactor comprising an sixth outlet, wherein the syngas production reactor is in fluid communication with the Fischer-Tropsch reactor via fifth connector, wherein the fifth connector is connected to the sixth outlet of the syngas production reactor and to the first inlet of the Fischer-Tropsch reactor.

In one aspect, the system further comprises a benzene conversion reactor comprising a seventh inlet, wherein the benzene conversion reactor is in fluid communication with the C5+ hydrocarbon conversion reactor via a sixth connector, wherein the sixth connector is connected to the seventh inlet of the benzene conversion reactor and to the fifth outlet of the C5+ hydrocarbon conversion reactor.

Isothermal and/or adiabatic fixed, moving, or fluidized bed reactors can be used as a Fischer-Tropsch reactor, which can carry out the Fischer-Tropsch process selective to the production of olefins. The Fischer-Tropsch reactor is configured to convert syngas to olefins.

The Fischer-Tropsch reactor can comprise one or more Fischer-Tropsch catalysts. Fischer-Tropsch catalysts are known in the art and can, for example, be Fe based catalysts and/or Co based catalysts and/or Ru based catalysts. Such catalysts are described in U.S. Pat. Nos. 4,088,671 and 4,207,248, which are incorporated herein by their entirety, specifically for their disclosure regarding Fischer-Tropsch catalysts.

A hydrocarbon separator is a separator that can separate hydrocarbons based on molecular weight. The hydrocarbon separator can be a series of separator designed to separate various hydrocarbons. For example, the hydrocarbon separator can be a deethanizer, depropanizer, debutanizer, or a combination thereof. The hydrocarbon separator is capable of separating a C2-C3 hydrocarbon stream from a first product stream produced from a Fischer-Tropsch process that converts syngas to olefins. The hydrocarbon separator is also capable of separating a C4 hydrocarbon stream from a first product stream produced from a Fischer-Tropsch process that converts syngas to olefins. The hydrocarbon separator is also capable of separating a C5+ hydrocarbon stream from a first product stream produced from a Fischer-Tropsch process that converts syngas to olefins. As such, the hydrocarbon separator allows for unconverted syngas to be separated from hydrocarbon so it can be recycled back into the Fischer-Tropsch reactor.

A deethanizer is known in the art. A deethanizer separates the C2 hydrocarbon stream, disclosed herein, from the hydrocarbon stream disclosed herein. The C2 hydrocarbon stream comprises ethylene and ethane. A deethanizer can be a fractionation column, which uses distillation separation technologies for hydrocarbon separation. Dethanizers are, for example, described in U.S. Pat. No. 7,554,002, European Patent 1035094, and U.S. Pat. No. 5,791,161, which are incorporated herein by their entirety, specifically for their disclosure regarding deethanizers. The C2 hydrocarbon stream can be subjected to a C2 splitter fractionation column to separate ethylene from ethane.

A depropanizer is known in the art. A depropanizer separates C3 hydrocarbons, disclosed herein, from other hydrocarbons, such as C2, C4, and C5+ hydrocarbons. A depropanizer can be a fractionation column, which uses distillation separation technologies for hydrocarbon separation. The C3 hydrocarbon stream comprises propylene and propane. Depropanizers are, for example, described in U.S. Pat. No. 6,291,734, which is incorporated herein by its entirety, specifically for its disclosure regarding depropanizers. The C3 hydrocarbon stream can be subjected to a C3 splitter fractionation column to separate propylene from propane.

A debutanizer is known in the art. A debutanizer separates C4 hydrocarbons, disclosed herein, from other hydrocarbons, such as C2-C3, and C5+ hydrocarbons. A debutanizer can be a fractionation column, which uses distillation separation technologies for hydrocarbon separation. Debutanizers are, for example, described in U.S. Pat. No. 6,291,734, which is incorporated herein by its entirety, specifically for its disclosure regarding debutanizers.

Thus, in one aspect, the first product stream can be first be subjected to process in a deethanizer, a process in a depropanizer, a process in a debutanizer, in such a process C5+ hydrocarbons would remain in the first product stream while at least a portion of the C2, C3, and C4, hydrocarbons would be removed from the first product stream.

A butadiene reactor is a vessel that is configured to convert butene (n-butene, such as 1-butene and 2-butene) to butadiene. The butadiene reactor is configured to carry out an oxidative dehydrogenation process of n-butene. The oxidative dehydrogenation process provides an attractive route for the production of butadiene as there are lower concentrations of undesirable compounds that need to be removed, such as isobutylene or isobutane. This reduces separation costs due to fewer similar boiling point compounds. Oxidative dehydrogenation is a process of dehydrogenation of n-butenes through contacting the paraffin with a catalyst. Oxidative dehydrogenation is an exothermic process that avoids some of the thermodynamic constraints of non-oxidative dehydrogenation processes by forming water as a by-product. In addition, carbon deposition is minimized, or eliminated, for a more stable catalytic process.

Oxidative dehydrogenation utilizes a catalyst such as vanadium oxide, molybdenum oxide, chromium oxide, or a vanadium-magnesium oxide catalyst, or even a combination of the metal oxides on a support. Supports can include aluminas, zirconia, titania, magnesia, and other refractory materials.

Oxidative dehydrogenation of butenes generates a crude butadiene stream which can have a high concentration of 1,3 butadiene, but generally also includes various levels of oxygenates, such as aldehydes The oxygenates can be further removed to avoid negative impacts on downstream processing units. As such, the use of oxidative dehydrogenation for the production of butadiene generates a crude product stream without significant amounts of isobutylene, isobutane or C3 and lighter hydrocarbons. Oxidative dehydrogenation of butenes is described in Published U.S. application 2014/0296589 to Krupa and in U.S. Pat. No. 7,034,195 to Schindler, which are both hereby incorporated by reference, specifically for their disclosure of oxidative dehydrogenation of butene.

A C2-C3 olefin separator is a separator that can separate C2-C3 olefins (ethylene and propylene) from C2-C3 paraffins (ethane and propane) and other products. The C2-C3 olefin separator can be a separator that cryogenically can separate C2-C3 olefins from C2-C3 paraffins. For example, the olefin separator can separate ethylene and propylene from a hydrocarbon stream. Olefin separators are known in the art and can also include distillation and membrane separation, or a combination thereof.

A C5+ hydrocarbon conversion reactor is a vessel that is configured to produce C5+ hydrocarbons, such as aromatics, such as, BTX, from hydrocarbons, such as, for example, C5-C12 hydrocarbons. The production of C5+ hydrocarbons, such as, for example, C6-C8 hydrocarbons or C5-C12 hydrocarbon, such as aromatics, such as BTX, is known in the art and is usually a catalytic process. For example, zeolite type catalyst can be used to convert hydrocarbons to aromatics, such as BTX. Accordingly the C5+ hydrocarbon conversion reactor can comprise a catalyst. For example, U.S. Pat. No. 5,968,343 to Drake discloses suitable catalysts and is incorporated herein by reference, specifically for its disclosure related to catalyst capable of producing aromatics, such as BTX.

During the conversion of C5+ hydrocarbons to aromatics, such as, BTX, C4-hydrocarbons, such as C2-C4 hydrocarbons, are also formed. These C4-hydrocarbons, such as C2-C4 hydrocarbons can be recycled back to the first product stream disclosed herein for further processing, as disclosed herein.

A benzene conversion reactor is a vessel that is configured to convert alkylated aromatics, such toluene or xylene, to benzene. Alkyl aromatics, such as toluene or xylene, can be dealkylated to lighter aromatics, such as benzene, by subjecting such alkyl aromatic in the presence of hydrogen to an elevated temperature and an elevated pressure for a controlled length of time. For example, the temperature of such process can be from 600° C. to 1,000° C., at a pressure of 5 to 70 bars. This process in known in the art and is described, for example, in U.S. Pat. No. 3,284,526 to Frayer and U.S. Pat. No. 4,463,206 to Derrien, which are both hereby incorporated by reference in their entirety, specifically for their disclosure of dealkylation of aromatics to benzene.

A syngas production reactor can produce syngas from one or more sources. Syngas can be produced from many sources, including natural gas, coal, biomass, or virtually any hydrocarbon feedstock, by reaction with steam or oxygen. For example, partial oxidation (POX) of methane (or hydrocarbons) is a non-catalytic, large-scale process to make syngas and yields syngas with $H_2$/CO ratio of about 2. In another example, the syngas reactor can convert natural gas into syngas. As such, the syngas production reactor can be an autothermal reforming (ATR) reactor which combines methane steam reforming and oxidation in one process. The heat needed for reforming is generated inside the reactor by oxididation of the feed gas (natural gas). ATR is also suitable for large-scale production of syngas for gas-to-liquids or large-scale methanol synthesis processes.

Optionally, in various aspects, the disclosed system can be operated or configured on an industrial scale. In one aspect, the reactors described herein can each be an industrial size reactor. For example, the Fischer-Tropsch reactor can be an industrial size reactor. In another example, the hydrocarbon separator can be an industrial size reactor. In yet another example, the deethanizer can be an industrial size fractionation column, which uses distillation separation technologies for hydrocarbon separation. In yet another example, the depropanizer can be an industrial size fractionation column, which uses distillation separation technologies for hydrocarbon separation. In yet another example, the debutanizer can be an industrial size fractionation column, which uses distillation separation technologies for hydrocarbon separation. In yet another example, the butadiene reactor can be an industrial size reactor. In yet another example, the C2-C3 olefin separator can be an industrial size reactor. In yet another example, the C5+ hydrocarbon conversion reactor can be an industrial size reactor. In yet another example, syngas production reactor can be an industrial size reactor.

The reactors disclosed herein can have a volume of at least 1,000 liters, 2,000 liters, 5,000 liters, or 20,000 liters. For example, the reactor can have a volume from 1,000 liter to 20,000 liters.

In one aspect, the Fischer-Tropsch reactor can have a volume of at least 1,000 liters, 2,000 liters, 5,000 liters, or 20,000 liters. For example, Fischer-Tropsch reactor can have a volume from 1,000 liter to 20,000 liters.

In one aspect, the hydrocarbon separator can have a volume of at least 1,000 liters, 2,000 liters, 5,000 liters, or 20,000 liters. For example, the hydrocarbon separator can have a volume from 1,000 liter to 20,000 liters.

In one aspect, the deethanizer can have a volume of at least 1,000 liters, 2,000 liters, 5,000 liters, or 20,000 liters. For example, the deethanizer can have a volume from 1,000 liter to 20,000 liters.

In one aspect, the depropanizer can have a volume of at least 1,000 liters, 2,000 liters, 5,000 liters, or 20,000 liters. For example, the depropanizer can have a volume from 1,000 liter to 20,000 liters.

In one aspect, the debutanizer can have a volume of at least 1,000 liters, 2,000 liters, 5,000 liters, or 20,000 liters. For example, the debutanizer can have a volume from 1,000 liter to 20,000 liters.

In one aspect, the butadiene reactor can have a volume of at least 1,000 liters, 2,000 liters, 5,000 liters, or 20,000 liters. For example, the butadiene reactor can have a volume from 1,000 liter to 20,000 liters.

In one aspect, the C2-C3 olefin separator can have a volume of at least 1,000 liters, 2,000 liters, 5,000 liters, or 20,000 liters. For example, the C2-C3 olefin separator can have a volume from 1,000 liter to 20,000 liters.

In one aspect, the C5+ hydrocarbon conversion reactor can have a volume of at least 1,000 liters, 2,000 liters, 5,000 liters, or 20,000 liters. For example, the C5+ hydrocarbon conversion reactor can have a volume from 1,000 liter to 20,000 liters.

In one aspect, the syngas production reactor can have a volume of at least 1,000 liters, 2,000 liters, 5,000 liters, or 20,000 liters. For example, the syngas production reactor can have a volume from 1,000 liter to 20,000 liters.

In one aspect, the benzene conversion reactor can have a volume of at least 1,000 liters, 2,000 liters, 5,000 liters, or 20,000 liters. For example, the benzene conversion reactor can have a volume from 1,000 liter to 20,000 liters.

In one aspect, the system is capable of producing at least about 25 liters, about 100 liters, about 500 liters, about 1,000 liters, about 10,000 liters, or from about 25 liters to about 10,000 liters of butadiene per hour.

In one aspect, the system is capable of producing at least about 25 liters, about 100 liters, about 500 liters, about 1,000 liters, about 10,000 liters, or from about 25 liters to about 10,000 liters of benzene per hour.

Now referring to the FIGURE, which shows a non-limiting exemplary aspect of the system and method disclosed herein. The FIGURE shows a system (100). The system has a syngas production reactor (102). The syngas production reactor (102) produces syngas (124) and is in fluid communication with a Fischer-Tropsch reactor (104). The Fischer-Tropsch reactor (104) converts the syngas (124) to a first product stream (126) and is in further fluid communication with a hydrocarbon separator (106). The hydrocarbon separator (106) separates (128, 132, 138) the first product stream (126) to a C2-C3 hydrocarbon stream (108), a C4 hydrocarbon stream (112), and a C5+ hydrocarbon stream (118). C2-C3 olefins (110) can be separated (130) from the C2-C3 hydrocarbon stream (108). Butane in the C4 hydrocarbon stream (112) can be converted (134) to butene (114). The butene (114) can be converted (136) to butadiene (116). The C5+ hydrocarbon stream (118) can be converted (140) to BTX (120). The toluene and xylene in the BTX (120) can be converted (142) to benzene (122). The process of converting the C5+ hydrocarbon stream (118) also produces C2-C4 hydrocarbons, which are recycled back (144) into the first product stream (126).

4. Methods

Also disclosed herein is a method of producing butadiene. In one aspect, the method can be performed by the system disclosed herein.

Disclosed herein is a method comprising the steps of: a) providing a first product stream comprising a C2-C3 hydrocarbon stream, a C4 hydrocarbon stream comprising butane and butene, and a C5+ hydrocarbon stream; b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream; and e) converting at least a portion of the butene in the C4 hydrocarbon stream to butadiene.

In one aspect, the method further comprises the step of producing the first product stream in Fischer-Tropsch process. The Fischer-Tropsch process can be performed in the Fischer-Tropsch reactor, as disclosed herein. As such, the first product stream is produced from a Fischer-Tropsch process.

In one aspect, steps of b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream occur simultaneously. In another aspect, steps of b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream occur in separate steps. In yet another aspect, steps of b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream occur in sequential order.

In one aspect, the step of converting at least a portion of the butene in the C4 hydrocarbon stream to butadiene is performed by an oxidative dehydrogenation process. Such an oxidative dehydrogenation process is well known in the art, as described herein.

In one aspect, method further comprises prior to step e), the step of converting at least a portion of the butane in the C4 hydrocarbon stream to butene. Thus, the butene being converted to butadiene can, in one aspect, be a mixture of the butene produced from the butane and the butene present in the first gas stream prior to processing. The process of converting butane to butene is known in the art.

In one aspect, the method further comprises the step of separating C2-C3 olefins from the C2-C3 hydrocarbon stream. The C2-C3 olefins comprise ethylene and propylene. The C2-C3 olefins can be separated using a C2-C3 olefin separator, such as C2-C3 splitters, which contains olefin separation columns containing a large number of separation stages. A C2 splitter can have over 90-100 stage and a C3 splitter can have over 150-200 stages. In some aspects, the C2-C3 splitters can comprise fractional trays, random or structured packing. The separated C2-C3 olefins are collected and further utilized in any process that is determined by one skilled in the art.

In one aspect, the C5+ hydrocarbon stream is a C5-C12 hydrocarbon stream. In another aspect, the C5+ hydrocarbon stream is a C6-C12 hydrocarbon stream. In another aspect, the C5+ hydrocarbon stream is a C6-C8 hydrocarbon stream.

In one aspect, the method further comprises the step of converting at least a portion of the C5+ hydrocarbon stream to BTX. The BTX can be chemical grade BTX comprising less than 5 wt % of hydrocarbons other than benzene, toluene and xylenes. The conversion of the at least a portion of the C5+ hydrocarbon stream to BTX can be performed in a C5+ hydrocarbon conversion reactor by use of a catalyst.

In one aspect, at least about 10 wt % of the C5+ hydrocarbon stream is converted to BTX. In another aspect, at least about 30 wt % of the C5+ hydrocarbon stream is converted to BTX. In yet another aspect, at least about 50 wt % of the C5+ hydrocarbon stream is converted to BTX. In yet another aspect, at least about 70 wt % of the C5+ hydrocarbon stream is converted to BTX. In yet another aspect, from about 10 wt % to about 99 wt %, such as from about 50 wt % to about 99 wt %, of the C5+ hydrocarbon stream is converted to BTX.

The step of converting at least a portion of the C5+ hydrocarbon stream to BTX further produces C2-C4 hydrocarbons which are recycled back into the first product stream.

In one aspect, the method further comprises the step of converting at least a portion of the toluene or xylene or combination thereof in the BTX to benzene. The step of converting at least a portion of the toluene or xylene or combination thereof in the BTX to benzene can be done in a dealkylation process by subjecting such alkyl aromatic in the presence of hydrogen to an elevated temperature and an elevated pressure for a controlled length of time. For example, dealkylation process can occur from 600° C. to 1,000° C., such as from 600° C. to 800° C., at a pressure of 5 to 70 bars, such as from 20 to 70 bars.

In one aspect, the first product stream is produced from a Fischer-Tropsch process converting syngas to olefins. The Fischer-Tropsch process can comprise syngas produced from natural gas.

In one aspect, the first product stream comprises at least about 1 wt % of the C4 hydrocarbon stream comprising butane and butene. In another aspect, the first product stream comprises at least about 5 wt % of the C4 hydrocarbon stream comprising butane and butene. In yet another aspect, the first product stream comprises at least about 10 wt % of the C4 hydrocarbon stream comprising butane and butene. In yet another aspect, the first product stream comprises at least about 20 wt % of the C4 hydrocarbon stream comprising butane and butene. In yet another aspect, the first product stream comprises at least about 30 wt % of the C4 hydrocarbon stream comprising butane and butene. In yet another aspect, the first product stream comprises at least about 40 wt % of the C4 hydrocarbon stream comprising butane and butene. In yet another aspect, the first product stream comprises at least about 50 wt % of the C4 hydrocarbon stream comprising butane and butene.

In one aspect, the first product stream comprises from about 1 wt % to about 80 wt % of the C4 hydrocarbon stream comprising butane and butene. In another aspect, the first product stream comprises from about 5 wt % to about 30 wt % of the C4 hydrocarbon stream comprising butane and butene. In another aspect, the first product stream comprises from about 10 wt % to about 20 wt % of the C4 hydrocarbon stream comprising butane and butene. In another aspect, the first product stream comprises from about 5 wt % to about 15 wt % of the C4 hydrocarbon stream comprising butane and butene.

In one aspect, the C4 hydrocarbon stream comprises at least about 60 wt % of butene. In another aspect, the C4 hydrocarbon stream comprises at least about 70 wt % of butene. In another aspect, the C4 hydrocarbon stream comprises at least about 80 wt % of butene.

In one aspect, the C4 hydrocarbon stream comprises at least from about 60 wt % to about 95 wt % of butene. In another aspect, the C4 hydrocarbon stream comprises at least from about 70 wt % to about 90 wt % of butene.

In one aspect, the C4 hydrocarbon stream comprises less than about 30 wt % of butane. In another example, the C4 hydrocarbon stream comprises less than about 25 wt % of butane. In yet another example, the C4 hydrocarbon stream comprises less than about 20 wt % of butane.

In one aspect, the C4 hydrocarbon stream comprises from about 10 wt % to about 30 wt % of butane and from about 90 wt % to about 70 wt % of butene.

In one aspect, the first product stream comprises at least about 1 wt % of the C2-C3 hydrocarbon stream. In another aspect, the first product stream comprises at least about 5 wt % of the C2-C3 hydrocarbon stream. In yet another aspect, the first product stream comprises at least about 10 wt % of the C2-C3 hydrocarbon stream. In yet another aspect, the first product stream comprises at least about 20 t % of the C2-C3 hydrocarbon stream. In yet another aspect, the first product stream comprises at least about 30 wt % of the C2-C3 hydrocarbon stream. In yet another aspect, the first product stream comprises at least about 40 wt % of the C2-C3 hydrocarbon stream. In yet another aspect, the first product stream comprises at least about 50 wt % of the C2-C3 hydrocarbon stream.

In one aspect, the first product stream comprises from about 1 wt % to about 80 wt % of the C2-C3 hydrocarbon stream. In another aspect, the first product stream comprises from about 5 wt % to about 30 wt % of the C2-C3 hydrocarbon stream. In another aspect, the first product stream comprises from about 10 wt % to about 20 wt % of the C2-C3 hydrocarbon stream.

In one aspect, the first product stream comprises at least about 1 wt % of the C5+ hydrocarbon stream. In another aspect, the first product stream comprises at least about 5 wt % of the C5+ hydrocarbon stream. In yet another aspect, the first product stream comprises at least about 10 wt % of the C5+ hydrocarbon stream. In yet another aspect, the first product stream comprises at least about 20 wt % of the C5+ hydrocarbon stream. In yet another aspect, the first product stream comprises at least about 30 wt % of the C5+ hydrocarbon stream. In yet another aspect, the first product stream comprises at least about 40 wt % of the C5+ hydrocarbon stream. In yet another aspect, the first product stream comprises at least about 50 wt % of the C5+ hydrocarbon stream.

In one aspect, the first product stream comprises from about 1 wt % to about 80 wt % of the C5+ hydrocarbon stream. In another aspect, the first product stream comprises from about 5 wt % to about 30 wt % of the C5+ hydrocarbon stream. In another aspect, the first product stream comprises from about 10 wt % to about 20 wt % of the C5+ hydrocarbon stream. In another aspect, the first product stream comprises from about 30 wt % to about 50 wt % of the C5+ hydrocarbon stream.

In one aspect, the method can produce at least 25 liters of butadiene per hour. In another aspect, the method can produce at least 100 liters of butadiene per hour. In yet another aspect, the method can produce at least 1,000 liters of butadiene per hour. In yet another aspect, the method can produce at least 10,000 liters of butadiene per hour. For example, the method can produce from 25 to 10.000 liters of butadiene per hour.

In one aspect, the method can produce at least 25 liters of BTX per hour. In another aspect, the method can produce at least 100 liters of BTX per hour. In yet another aspect, the method can produce at least 1,000 liters of BTX per hour. In yet another aspect, the method can produce at least 10,000 liters of BTX per hour. For example, the method can produce from 25 to 10,000 liters of BTX per hour.

In one aspect, the method can produce at least 25 liters of benzene per hour. In another aspect, the method can produce at least 100 liters of benzene per hour. In yet another aspect, the method can produce at least 1,000 liters of benzene per hour. In yet another aspect, the method can produce at least 10,000 liters of benzene per hour. For example, the method can produce from 25 to 10,000 liters of benzene per hour.

5. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of: a) providing a first product stream comprising a C2-C3 hydrocarbon stream, a C4 hydrocarbon stream comprising butane and butene, and a C5+ hydrocarbon stream; b) separating at least a portion of the C2-C3 hydrocarbon stream from the first product stream; c) separating at least a portion of the C4 hydrocarbon stream comprising butane and butene from the first product stream; d) separating at least a portion of the C5+ hydrocarbon stream from the first product stream; and e) converting at least a portion of the butene in the C4 hydrocarbon stream to butadiene.

Aspect 2: The method of aspect 1, wherein the first product stream comprises at least about 1 wt % of the C2-C3 hydrocarbon stream.

Aspect 3: The method of aspect 1, wherein the first product stream comprises at least about 1 wt % of the C4 hydrocarbon stream comprising butane and butene.

Aspect 4: The method of aspect 1, wherein the first product stream comprises at least about 1 wt % of the C5+ hydrocarbon stream.

Aspect 5: The method of aspect 1, wherein the first product stream comprises from about 10 wt % to about 30 wt ° % of the C2-C3 hydrocarbon stream.

Aspect 6: The method of aspect 1, wherein the first product stream comprises from about 5 wt % to about 15 wt % of the C4 hydrocarbon stream comprising butane and butene.

Aspect 7: The method of aspect 1, wherein the first product stream comprises from about 30 wt % to about 50 wt % of the C5+ hydrocarbon stream.

Aspect 8: The method of any one of claims 1-7, wherein steps b), c), and d) occur simultaneously.

Aspect 9: The method of any one of aspects 1-8, wherein the method further comprises prior to step e), the step of converting at least a portion of the butane in the C4 hydrocarbon stream to butene.

Aspect 10: The method of any one of aspects 1-9, wherein the method further comprises after step b) the step of separating C2-C3 olefins from the C2-C3 hydrocarbon stream.

Aspect 11: The method of any one of aspects 1-10, wherein the C5+ hydrocarbon stream is a C5-C12 hydrocarbon stream.

Aspect 12: The method of any one of aspects 1-11, wherein the method further comprises the step of converting at least a portion of the C5+ hydrocarbon stream to BTX.

Aspect 13: The method of aspect 12, wherein the BTX is chemical grade BTX comprising less than 5 wt % of hydrocarbons other than benzene, toluene and xylene.

Aspect 14: The method of any one of aspects 1-13, wherein the C4 hydrocarbon stream comprises at least 60 wt % of butene.

Aspect 15: The method of any one of aspects 1-13, wherein the C4 hydrocarbon stream comprises less than 40 wt % of butane.

Aspect 16: The method of any one of aspects 12-15, wherein the step of converting at least a portion of the C5+ hydrocarbon stream to BTX further produces C2-C4 hydrocarbons which are recycled back into the first product stream.

Aspect 17: The method of any one of aspects 1-16, wherein the method further comprises the step of converting at least a portion of the toluene or xylene or combination thereof in the BTX to benzene.

Aspect 18: The method of aspect 17, wherein the method further comprises the step of separating out benzene from the BTX.

Aspect 19: The method of any one of aspects 1-18, wherein the Fischer-Tropsch process comprises syngas produced from natural gas.

Aspect 20: A system comprising: a) a Fischer-Tropsch reactor comprising a first inlet and a first outlet; b) a hydrocarbon separator comprising a second inlet, second' outlet, a second" outlet, and a second'" outlet; c) a butadiene reactor comprising a third inlet and a third outlet, d) a C2-C3 olefin separator comprising a fourth inlet and a fourth outlet; and e) a C5+ hydrocarbon conversion reactor comprising a fifth inlet and a fifth outlet, wherein the Fischer-Tropsch reactor is in fluid communication with the hydrocarbon separator via a first connector, wherein the first connector is connected to the first outlet of the Fischer-Tropsch reactor and to the second inlet of the hydrocarbon separator, wherein the hydrocarbon separator is in fluid communication with the butadiene reactor via a second connector, wherein the second connector is connected to the second' outlet of the hydrocarbon separator and to the third inlet of the butadiene reactor, wherein the hydrocarbon separator is in fluid communication with the C2-C3 olefin separator via a third connector, wherein the third connector is connected to the second" outlet of the hydrocarbon separator and to the fourth inlet of the C2-C3 olefin separator, wherein the hydrocarbon separator is in fluid communication with the C5+ hydrocarbon conversion reactor via a fourth connector, wherein the fourth connector is connected to the second'" outlet of the hydrocarbon separator and to the fifth inlet of the C5+ hydrocarbon conversion reactor.

Aspect 21: The system of aspect 20, wherein the system further comprises a syngas production reactor comprising an sixth outlet, wherein the syngas production reactor is in fluid communication with the Fischer-Tropsch reactor via fifth connector, wherein the fifth connector is connected to the sixth outlet of the syngas production reactor and to the first inlet of the Fischer-Tropsch reactor.

Aspect 22: The system of aspect 20 or 21, wherein the system further comprises a benzene conversion reactor comprising a seventh inlet, wherein the benzene conversion reactor is in fluid communication with the C5+ hydrocarbon conversion reactor via a sixth connector, wherein the sixth connector is connected to the seventh inlet of the benzene conversion reactor and to the fifth outlet of the C5+ hydrocarbon conversion reactor.

Aspect 23: The system of any one of aspects 20-22, wherein the system is on an industrial scale.

What is claimed is:

1. A method comprising the steps of:
   a) producing a first product steam via a Fischer-Tropsch process, wherein the first product stream comprises a C2-C3 hydrocarbon stream, a C4 hydrocarbon stream comprising butane and butene, and a C5+ hydrocarbon stream comprising at least a C6 hydrocarbon;
   b) separating at least a portion of the C2-C3 hydrocarbon stream from the first product stream;
   c) separating at least a portion of the C4 hydrocarbon stream comprising butane and butene from the first product stream;
   d1) separating at least a portion of the C5+ hydrocarbon stream from the first product stream;
   d2) converting at least a portion of the butane in the C4 hydrocarbon stream to butene;
   e) converting at least a portion of the butene in the C4 hydrocarbon stream and from step d2) to butadiene; and
   f) converting the at least a portion of the C5+ hydrocarbon stream to BTX.

2. The method of claim 1, wherein the first product stream comprises at least about 1 wt % of the C2-C3 hydrocarbon stream.

3. The method of claim 1, wherein the first product stream comprises at least about 1 wt % of the C4 hydrocarbon stream comprising butane and butene.

4. The method of claim 1, wherein the first product stream comprises at least about 1 wt % of the C5+ hydrocarbon stream.

5. The method of claim 1, wherein the first product stream comprises from about 10 wt % to about 30 wt % of the C2-C3 hydrocarbon stream.

6. The method of claim 1, wherein the first product stream comprises from about 5 wt % to about 15 wt % of the C4 hydrocarbon stream comprising butane and butene.

7. The method of claim 1, wherein the method further comprises after step b) a step of separating C2-C3 olefins from the at least a portion of the C2-C3 hydrocarbon stream separated from the first product stream.

8. The method of claim 1, wherein the C5+ hydrocarbon stream is a C5-C12 hydrocarbon stream.

9. The method of claim 1, wherein the BTX is chemical grade BTX comprising less than 5 wt % of hydrocarbons other than benzene, toluene and xylene.

10. The method of claim 1, wherein the C4 hydrocarbon stream comprises at least 60 wt % of butene.

11. The method of claim 1, wherein the step of converting at least a portion of the C5+ hydrocarbon stream to BTX further produces C2-C4 hydrocarbons which are recycled back into the first product stream.

12. The method of claim 1, wherein the method further comprises a step of converting at least a portion of the toluene or xylene or combination thereof in the BTX to benzene.

13. The method of claim 12, wherein the method further comprises a step of separating out benzene from the BTX.

14. The method of claim 1, wherein step b) is performed by distillation, membrane separation, or a combination thereof.

15. A method comprising the steps of:
a) producing a first product steam via a Fischer-Tropsch process, wherein the first product stream comprises a C2-C3 hydrocarbon stream, a C4 hydrocarbon stream comprising butane and butene, and a C5+ hydrocarbon stream comprising at least a C6 hydrocarbon;
b) separating at least a portion of the C2-C3 hydrocarbon stream from the first product stream;
c) separating at least a portion of the C4 hydrocarbon stream comprising butane and butene from the first product stream;
d1) separating at least a portion of the C5+ hydrocarbon stream from the first product stream;
d2) converting at least a portion of the butane in the C4 hydrocarbon stream to butene; and
e) converting at least a portion of the butene in the C4 hydrocarbon stream and from step d2) to butadiene wherein the first product stream comprises from about 30 wt % to about 50 wt % of the C5+ hydrocarbon stream.

16. A method comprising the steps of:
a) producing a first product steam via a Fischer-Tropsch process, wherein the first product stream comprises a C2-C3 hydrocarbon stream, a C4 hydrocarbon stream comprising butane and butene, and a C5+ hydrocarbon stream comprising at least a C6 hydrocarbon;
b) separating at least a portion of the C2-C3 hydrocarbon stream from the first product stream;
c) separating at least a portion of the C4 hydrocarbon stream comprising butane and butene from the first product stream;
d1) separating at least a portion of the C5+ hydrocarbon stream from the first product stream;
d2) converting at least a portion of the butane in the C4 hydrocarbon stream to butene; and
e) converting at least a portion of the butene in the C4 hydrocarbon stream and from step d2) to butadiene wherein steps b), c), and d1) occur simultaneously.

* * * * *

UNITED STATES PATENT AND TRADEMARK OFFICE
CERTIFICATE OF CORRECTION

PATENT NO. : 10,927,058 B2  
APPLICATION NO. : 15/573607  
DATED : February 23, 2021  
INVENTOR(S) : Thabet Mohammed Al-Qahtani et al.

Page 1 of 1

It is certified that error appears in the above-identified patent and that said Letters Patent is hereby corrected as shown below:

In the Claims

At Column 16, Claim number 15, starting at Line number 6, delete "butadiene wherein" and replace with --butadiene, wherein--.
At Column 16, Claim number 16, starting at Line number 26, delete "butadiene wherein" and replace with --butadiene, wherein--.

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*